United States Patent
Dassen et al.

(10) Patent No.: US 7,183,443 B2
(45) Date of Patent: Feb. 27, 2007

(54) PROCESS FOR THE PREPARATION OF ENANTIOMERICALLY ENRICHED COMPOUNDS

(75) Inventors: Bernardus Henricus Nicolaas Dassen, Heerlen (NL); Bernardus Kaptein, Sittard (NL); Quirinus Bernardus Broxterman, Munstergeleen (NL)

(73) Assignee: DSM IP Assets B.V., Te Heerlen (NL)

( * ) Notice: Subject to any disclaimer, the term of this patent is extended or adjusted under 35 U.S.C. 154(b) by 203 days.

(21) Appl. No.: 10/510,660

(22) PCT Filed: Apr. 7, 2003

(86) PCT No.: PCT/NL03/00262

§ 371 (c)(1),
(2), (4) Date: Oct. 7, 2004

(87) PCT Pub. No.: WO03/087033

PCT Pub. Date: Oct. 23, 2003

(65) Prior Publication Data

US 2005/0215822 A1    Sep. 29, 2005

(30) Foreign Application Priority Data

Apr. 9, 2002    (EP) .................... 02076383

(51) Int. Cl.
*C07C 45/44* (2006.01)
*C07C 29/48* (2006.01)

(52) U.S. Cl. .............. 568/467; 568/424; 568/426; 568/704; 568/705; 568/814; 568/861; 568/873; 568/881; 568/885; 568/903; 568/914

(58) Field of Classification Search .............. None
See application file for complete search history.

(56) References Cited

U.S. PATENT DOCUMENTS

| 4,072,698 A | 2/1978 | Hylton et al. ........... 260/465 |
| 4,683,324 A | 7/1987 | Gastrock et al. .......... 558/354 |

FOREIGN PATENT DOCUMENTS

| EP | 1013773 | 6/2000 |
| FR | 2141354 | 1/1973 |
| JP | 79/48729 | 4/1979 |

OTHER PUBLICATIONS

Database CASREACT 107:7477, Anales de Quimica, Serie C: Quimica Organica y Bioquimica (1986), 82(1), p. 11-17 (abstract).*
Perez et al., Anales de Quimica, Serie C: Quimica Organica y Bioquimica (1986), 82(1), p. 11-17.*
Umio, Journal of the Pahrmaceutical Society of Japan (1958), 78, p. 1072-1074.*
Boesten et al., Org. Lett. (2001) 3:1121-1124.
Bose et al., Synthesis (1999) 1724-1726.
Byrne et al., Tetrahedron Lett. (2000) 41:873-876.
Corey et al., Org. Lett. (1999) 1:157-160.
International Search Report for PCT/NL03/00262, mailed on Aug. 26, 2003, 2 pages.
Ishitani et al., Angew. Chem. (1998) 37:3186-3188.
Kawashiro et al., Chem. Lett. (1976) 417-418.
Krueger et al., J. Am. Chem. Soc. (1999) 121:4284-4285.
Layh et al., Appl. Microbiol. Biotechn. (1997) 47:668-674.
López-Serrano et al., Tetrahedron Asymm. (2001) 12:219-228.
Matthews et al., Tetrahedron Lett. (1989) 30(38):5157-5158.
Nakai et al., Bull. Inst. Chem. Res. Kyoto Univ. (1992) 70:333-337.
Podlech et al., Houben-Weyl Methods of Organic Chemistry, 4$^{th}$ ed., vol. 22a, (2002) pp. 41-165.
Reinhold et al., J. Org. Chem. (1968) 33:1209-1213.
Romeo et al., Terahedron Lett. (1971) 21:1799-1802.
Rossi et al., J. Org. Chem. (1978) 43:2576-2581.
Sigman and Jacobsen, J. Am. Chem. Soc. (1998) 120:4901-4902.
Sigman and Jacobsen, J. Am. Chem. Soc. (1998) 120:5315-5316.
Stout et al., J. Org. Chem. (1983) 48:5369-5373.
Tinapp, Archiv Der Pharmazie (1982) 315(4):307-311.
Umio, J. of the Pharmaceutical Society of Japan (1958) 78:1072-1074.

* cited by examiner

*Primary Examiner*—Brian Davis
(74) *Attorney, Agent, or Firm*—Nixon & Vanderhye P.C.

(57) ABSTRACT

Process for the preparation of enantiomerically enriched amino aldehydes and amino alcohols, wherein a corresponding enantiomerically enriched amino nitrile is subjected to hydrogenation in the presence of hydrogen, a hydrogenation catalyst, preferably a Pd-catalyst and a mineral acid. For the preparation of an amino aldehyde hydrogen preferably is present at a hydrogen-pressure between 0.1 and 2 MPa, in particular between 0.5 and 1 MPa. The amino aldehyde preferably is isolated in the form of a chemically and configurationally stable derivative. For the preparation of an amino alcohol, preferably at least during part of the hydrogenation hydrogen is present at a hydrogen-pressure between 2 and 10 MPa, in particular between 4 and 6 MPa. In a preferred embodiment the hydrogen-pressure initially is between 0.5 and 2 MPa and subsequently, after most of the nitrile starting material is converted, the hydrogen pressure is increased to a value between 2 and 10 MPa. The enantiomerically enriched nitrile starting material may a.o. be prepared by enzymatic resolution, classical resolution, resolution via preferential crystallization, diastereomeric synthesis, catalytic asymmetric synthesis or dehydratation of amino acid amides.

10 Claims, No Drawings

PROCESS FOR THE PREPARATION OF ENANTIOMERICALLY ENRICHED COMPOUNDS

CROSS-REFERENCE TO RELATED APPLICATIONS

This application is the national phase of PCT application PCT/NL03/00262 having an international filing date of 7 Apr. 2003, which claims priority from European application 02076383.5 filed 9 Apr. 2002. The contents of these documents are incorporated herein by reference.

The invention relates to a process for the preparation of an enantiomerically enriched compound of formula 1

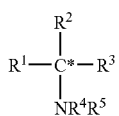

(1)

or a salt thereof, wherein:

C* represents an asymmetric carbon atom;

$R^1$ and $R^2$ are different from each other, and, each independently, represent H, a substituted or unsubstituted alkyl or aryl group;

$R^3$ represents $CH_2OH$ or an optionally protected CHO group;

$R^5$ represents H, a substituted or unsubstituted alkyl or aryl group;

$R^4$ represents H or $C(=O)R^6$ wherein $R^6$ represents H, a substituted or unsubstituted alkyl, aryl or alkoxy group, $R^4$ represents an amine protecting group, or $R^4$ and $R^5$ form together with the N to which they are attached a cyclic imide group wherein an enantiomerically enriched compound with formula 2

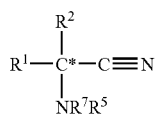

(2)

or a salt thereof, wherein C*, $R^1$, $R^2$, $R^3$, and $R^5$ are as defined above and $R^7$ represents H or $C(=O)R^6$ wherein $R^6$ is defined above, $R^7$ represents an amine protecting group, or $R^5$ and $R^7$ form together with the N to which they are attached a cyclic imide group is subjected to hydrogenation in the presence of hydrogen, a hydrogenation catalyst and a mineral acid.

Known in the art are processes for the preparation of enantiomerically enriched β-amino alcohols by hydride reduction of the corresponding enantiomerically enriched α-amino acids or derivatives thereof, for instance amides, esters or (mixed) anhydrides, using hydrides, for instance $LiAlH_4$ or $NaBH_4$, optionally in the presence of a Lewis acid or a Brönsted acid, for instance $H_2SO_4$. The hydrides used, however, are expensive. Moreover, such reduction processes require specific safety measures and are difficult to scale up. In addition, the starting material used (amino acid, amino acid ester, amino acid amide and (mixed) amino acid anhydride) is, when using Strecker synthesis, prepared in subsequent synthesis steps starting from the corresponding amino nitrile. Consequently such processes require more reaction steps.

For the preparation of enantiomerically enriched (N-protected) amino aldehydes processes are known in the art that are based on hydride reduction of amino acid esters with DIBAL-H or $LiAlH_4$ reduction of Weinreb amides; and processes based on the oxidation, for instance Swern oxidation, TEMPO oxidation or periodane oxidation of amino alcohols. These known processes for the preparation of amino aldehydes suffer from the same disadvantages, like safety requirements, expensive starting materials, a large number of reaction steps and/or difficult to scale up, as the above mentioned process for the preparation of enantiomerically enriched amino alcohols.

The present invention now provides a commercially attractive route for the preparation of a broad range of enantiomerically enriched compounds according to formula 1.

This is achieved according to the invention by hydrogenation of a compound with formula 2 under conditions suitable to obtain the desired compound with formula 1.

Surprisingly the nitrites with formula 2 can easily and with good yield be converted into the corresponding compound with formula 1, without substantial racemization. The enantiomerically enriched nitrites with formula 2, moreover, can be easily prepared, using methods known in the art. Accordingly, in combination, a short, commercially attractive concept for the preparation of the important chiral building blocks of formula 1 is obtained.

With the process according to the invention enantiomerically enriched compounds with formula 1 can be prepared, such as β-amino alcohols and α-amino aldehydes, starting from a corresponding nitrile with formula 2. $R^1$ and $R^2$ of formula 1 and 2, each independently represent H or a substituted or unsubstituted alkyl or aryl group with for instance 1–40, preferably 1–20 C-atoms. The alkyl or (hetero) aryl group may be substituted with 1 or more substituents. Suitable substituents are for instance alkyl, alkoxy, halogen, aryl, amino or hydroxy groups with, for instance, 0–10 C-atoms. $R^4$ represents H or $C(=O)R^6$ as described above, for instance an acylgroup with e.g. 1–10 C-atoms, in particular a formyl, acetyl or substituted acetyl group, in particular chloroacetyl, phenacetyl, methoxyacetyl or trifluoroacetyl, a carbamate group with e.g. 1–20 C-atoms, in particular benzyloxycarbonyl (Z), t-butoxycarbonyl (Boc) or 9-fluorenylmethyloxycarbonyl (Fmoc), or any other protecting group used in peptide coupling chemistry, as for instance described in J. Podlech et al. in Houben-Weyl Methods of Organic Chemistry (4th. Editon), Vol 22a, Thieme, Stuttgart, 2002, pp 41–165. $R^7$ most preferably is chosen in relation to hydrogenation conditions and compatible with the process and process conditions for the preparation of the specific enantiomerically enriched compound with formula 2 that is chosen as starting material. For instance $R^7$ preferably represents an acetyl group when an acylase is used in the preparation of the enantiomerically enriched starting material with formula 2, or a phenacetyl group when a Pen acylase is used or a formyl group when a peptide deformylase (PDF; enzymes having formyl methionine peptide deformylase activity) is used. $R^4$ may be the same as $R^7$; alternatively if the group $R^7$ (where $R^7$ does not represent H) is removed under the conditions of the hydrogenation step, $R^4$ is not equal to $R^7$ and represents H. The nitrile starting material with formula 2 and the compounds obtained with the process according to the invention preferably have an enantiomeric excess larger than 80%, more preferably larger than 90%, most preferably larger than 95%, in particular larger than 98%.

The enantiomerically enriched amino nitriles may for instance be prepared by (precursor) fermentation or by enzymatic resolution of N-formyl amino nitriles using a PDF as, for instance described in EP 1,013,773; or by acylation of amino nitriles using acylases as, for instance described in K. Nakai et al., Bull. Inst. Chem. Res. Kyoto Univ. (1992) 70, 333–337, and in R. A. Sheldon et al., Tetrahedron Asymm. (2001) 12, 219–228 and using PenG acylase as described in A. Romeo et al., Tetrahedron Lett. (1971) 21, 1799–1802 and in J. Org. Chem. (1 978), 43, 2576–81, or by using nitrilases, as for instance described in N. Layh et al., Appl. Microbiol. Biotechn. (1997) 47, 668–674, or using classical resolution (via diasteromeric salt formation) or crystallization induced asymmetric transformation, as for instance described in U.S. Pat. No. 4,683,324; J. Org. Chem. (1968) 33, 1209–1213 (disubstituted amino nitriles) and in FR 2,141,354; U.S. Pat. No. 4,072,698; JP 79/48,729; Hung. Teljes 7587; Hung. Teljes 16,078 (aromatic amino nitriles); or by resolution via preferential crystallisation, as for instance described in J. Org. Chem. (1968) 33, 1209–1213 (N-acetyl amino nitrile for MethylDOPA; or by diastereomeric synthesis, as for instance described in W H J Boesten, Org. Lett. (2001) 3, 1121–1124; J. Org. Chem. (1983) 48, 5369–5373; or by catalytic asymmetric synthesis, as for instance described in E. Jacobsen, J. Am. Chem. Soc. (1998) 118, 4901–4902 and ibid. (1998) 120, 5315–5316, E. J. Corey, Org. Lett. (1999) 1, 157–160, A. H. Hoveyda, J. Am. Chem. Soc. (1999) 121, 4284–4285, S. Kobayashi, Angew. Chem. (1998) 37, 3186–3188 (α-H amino nitrites), or Y. Vallée, Tetrahedron Lett. (2000) 41, 873–876 (disubstituted amino nitriles); or by dehydratation of amino acid amides, as for instance described in K. Kawashiro, Chem. Lett. (1976) 417–418 (with POCl3), W H J Boesten, Org. Lett. (2001) 3, 1121–1124 (Vilsmeier reagent) or Bose, Synthesis (1999) 1724–1726 (with $Bu_2SnO$).

The hydrogenation reaction will be carried out using a hydrogenation catalyst for instance a Pd-catalyst, in particular Pd/C, PdO or Pd/BaSO4, Pt-catalyst in particular Pt/C or Pt-oxide, Raney Ni, Raney Co, a Ru- or a Rh-catalyst. Preferably the hydrogenation reaction is carried out in the presence of an aqueous solvent, for instance water, a water-alcohol or a water-dioxane mixture, in the presence of a mineral acid for instance HCl or $H_2SO_4$. The amount of mineral acid to be used is preferably 1–4 equivents calculated with respect to the molar amount of the amino nitrile, preferably 1.5–2.5 equivalents.

The hydrogenation reaction will be carried out in the presence of hydrogen. In the hydrogenation reaction generally a mixture of the corresponding enantiomerically enriched alcohol and the enantiomerically enriched amino aldehyde will be prepared. Under a given set of hydrogenation conditions the ratio between these products largely is determined by the choice of the hydrogen pressure; at a larger hydrogen-pressure more of the enantiomerically enriched amino alcohol is prepared, and at lower hydrogen-pressure more of the enantiomerically enriched amino aldehyde is prepared. For the preparation of enantiomerically enriched amino aldehydes the hydrogen pressure preferably is chosen between 0.1 and 2 MPa, in particular between 0.5 and 1 MPa. For the preparation of enantiomerically enriched amino alcohols the hydrogen pressure is preferably chosen between 3 and 10 MPa, in particular between 4 and 6 MPa. Optionally the hydrogen pressure in the preparation of amino alcohols initially may be chosen lower until most, preferably virtually all of the nitrile starting material is converted (to aldehyde), followed by increasing the hydrogen-pressure whether or not under addition of an additional amount of catalyst. The person skilled in the art will easily be able to determine the optimum hydrogen-pressure and catalyst loading for his particular compound. Of course in stead of hydrogen also a suitable hydrogen donor may be used, for instance formic acid, ammonium formate or triethyl ammonium formate.

In the process according to the invention often also small amounts of diamines will be formed as a byproduct of the hydrogenation of amino nitriles to amino aldehydes or amino alcohols. It is for instance described in the art that the hydrogenation of N-protected amino nitrites in alcoholic ammonia over a Raney-Ni or Pd/C catalyst for example leads to mono-protected diamines. By optimization of the process conditions the formation of byproduct can be reduced. Furthermore, eventual byproducts may be removed by standard techniques like, for example, crystallization, selective extraction, selective complexation or destillation.

The enantiomerically enriched amino alcohols can be purified, for instance, by distillation or crystallisation of the free amino alcohol, its salt of a mineral acid eg. its HCl-salt, or its salt of an organic acid eg. its oxalate salt, tartrate-salt or malate-salt.

Amino aldehydes as such are known to be relatively unstable and to racemize easily, as a rule it is advantageous to isolate and purify the amino aldehydes as a chemically and configurationally stable derivative. After the hydrogenation reaction the amino aldehyde in the reaction mixture can be transformed in situ into a stable amino aldehyde derivative, for instance its N,N-dibenzylated derivative, bisulfite adduct, acetal, oxime, hydrazone, cyanohydrine or amino nitrile by reaction with for instance a benzylating agent, $NaHSO_3$, an alcohol, diol or ortho ester, $NH_2OR$ (with R is e.g. H or C1–C10 alkyl), $NH_2NHR$ (with R is e.g. H, C1–C10 alkyl, C6–C10 aryl, C1–C10 acyl or carbamoyl) HCN or $HCN/NHR_2$ (wherein each R independently may represent H or C1–C10 alkyl or both R groups together with the N to which they are attached form a alifatic (hetero) cyclic ring with 4–6 C-atoms) and isolated as such by for example crystallization or distillation. In case $R_4$=H, the amino aldehyde can be isolated as its stable salt in the form of a hydrate, hemiacetal or acetal.

The invention will further be elucidated using the following examples, without, however, being restricted thereby.

EXAMPLE 1

Strecker Synthesis of
rac-2-amino-3-phenylpropionitrile

A 30 wt % solution of sodium cyanide (653 g, 4.0 mol) at 25° C. was saturated with ammonia gas at 0.15 MPa. In 30 min time 240 g (4.0 mol) of acetic acid was added, followed by the addition of 534 g (4.0 mol) of phenylacetaldehyde (80–90%) in 45 min. After stirring for 4 h at 35° C., the reaction mixture was extracted with 2 L of $CH_2Cl_2$. The organic layer was evaporated and the residue dissolved in 4.5 L of diethyl ether. To this solution 3–3.5 mol of saturated HCl in dioxan was added. The precipitated rac-2-amino-3-phenylpropionitrile.HCl was filtered and washed with ether (yield 80–85%).

EXAMPLE 2

Diastereomeric Resolution of
rac-2-amino-3-phenylpropionitrile
(phenylalaninonitril)

A solution of 182.5 g (1 mol) of rac-2-amino-3-phenyl-propionitrile.HCl-salt (prepared by Strecker synthesis) and 170.4 g (0.6 mol) of N-4-chlorobenzoyl-L-glutamic acid in 2.2 L of absolute EtOH at room temperature was slowly added 60.6 g (0.6 mol) of $Et_3N$. The mixture was stirred for additional 2 h. The precipitate was filtered and washed with 500 ml of ethanol. To the solid was added 2 L of ethyl acetate and 1 L of water and the solution was acidified with concentrated HCl solution to pH 1. The aqueous layer was separated and concentrated in vacuo. The remaining water was removed by azeotropic distillation with i-PrOH. The remaining solid was dissolved in 500 mL of MeOH. To this stirred solution 2 L of $Et_2O$ was slowly added. The precipitated white solid was filtered off, washed with ether and dried. Yield: 50.7 g (56%) of (R)-2-amino-3-phenylpropionitrile.HCl-salt, e.e.>97.5% (HPLC).

EXAMPLE 3

Diastereomeric Resolution of
rac-2-amino-3-methylbutyronitrile (valinonitrile)

To a solution of 40 g (0.30 mol) of rac-2-amino-3-methylbutyronitrile.HCl (prepared by Strecker synthesis as described above) in 1.1 L of MeOH/toluene 70:30 was added 30 g (0.30 mol) of $Et_3N$ and 45 g (0.30 mol) of D-(−)-tartaric acid. After stirring for 70 h at ambient temperature the mixture was cooled and filtered. The residue was dissolved in water/$CH_2Cl_2$ and neutralized with dilluted NaOH solution to pH 9. The $CH_2Cl_2$ was separated and extracted with diluted HCl solution (pH 1). After evaporation of the water layer and azeotropic removal of water with i-PrOH, (R)-2-amino-3-methylbutyronitrile.HCl was obtained in a low yield and 71% e.e.

EXAMPLE 4

Diastereomeric Resolution of
rac-2-amino-4-methylvaleronitrile (leucinonitrile)

The HCl-salt of rac-2-amino-4-methylvaleronitrile (prepared by Strecker synthesis as described above) was liberated by neutralization in water/$CH_2Cl_2$ to pH 9. After extraction the $CH_2Cl_2$ layer was evaporated and the residue dissolved in 500 mL MeOH. To the MeOH solution was added 45 g (0.30 mol) of L-(+)-tartaric acid, followed by 400 mL of toluene. After stirring for 24 h at ambient temperature, the precipitate was filtered. This diastereomeric salt was dissolved in water/$CH_2Cl_2$ and neutralized with a dilluted NaOH solution to pH 9. The $CH_2Cl_2$ was separated and extracted with diluted HCl solution (pH 1). After evaporation of the water layer and azeotropic removal of water with i-PrOH, (S)-2-amino-4-methylvaleronitrile.HCl was obtained in >50% yield and 25% e.e.

EXAMPLE 5

Diastereomeric Resolution of
rac-2-amino-2,3-dimethylbutyronitrile
(α-methylvalinonitrile)

The HCl-salt of 2-amino-2,3-dimethylbutyronitrile (prepared by Strecker synthesis as described above) was liberated by neutralization in water/$CH_2Cl_2$ to pH 8.5 with diluted NaOH solution. After the extraction the $CH_2Cl_2$ layer was evaporated and the residue dissolved in 200 mL MeOH. To this solution was added a solution of 45 g (0.30 mol) of L-(+)-tartaric acid in 200 mL of MeOH. The suspension was stirred for 48 h at ambient temperature and filtered. The diastereomeric salt was isolated 74% yield and 89% e.e.(S). This salt was dissolved in water/$CH_2Cl_2$ and neutralized with a NaOH solution to pH 10. The $CH_2Cl_2$ was separated and extracted with diluted HCl solution (pH 1). After evaporation of the water layer and azeotropic removal of water with i-PrOH, (S)-2-amino-2,3-dimethylbutyronitrile.HCl was obtained in 91% e.e.

EXAMPLE 6

Peptide deformylase (PDF) Resolution of
rac-2-amino-3-phenylpropionitrile

To 27 mL buffer-solution of pH 7.4 (containing 0.1 mg/mL catalase, 6 M sodium formate, 0.25 M sodium chloride and 100 mM MOPS buffer) was added 25 mg PDF and 1.0 g rac-2-amino-3-phenylpropionitrile.HCl-salt. This solution was adjusted to pH 6.7. After 20 h of shaking at ambient temperature the reaction was stopped at 38% conversion. A small amount of the heterogeneous reaction mixture was extracted with $CH_2Cl_2$. (S)-2-Formamido-3-phenylpropionitrile with e.e.>99% (HPLC) was isolated from the organic layer. The precipitate in the remaining part of the reaction mixture was filtered yielding (S)-2-formamido-3-phenylpropionitrile (e.e.>99.5%) as a white solid.

EXAMPLE 7

PDF Resolution of
rac-2-amino-4-methylvaleronitrile

To a solution of 145 mg of 2-amino-4-methylvaleronitrile.HCl in 12.5 mL buffer-solution of pH 7.4 (0.1 mg/mL catalase, 6 M sodium formate, 0.25 M sodium chloride and 100 mM MOPS buffer) 25 mg PDF was added. After 2.5 h at ambient temperature a conversion of 39% was reached. The e.e. of the remaining (R)-amino nitrile was 63% and the e.e. of the (S)-2-formamido-4-methylvaleronitrile was>98% (HPLC). The product could be isolated by extraction with $CH_2Cl_2$ as described above.

EXAMPLE 8

Screening of the Enzymatic Resolution of
rac-2-amino-3-phenylpropionitrile in Organic
Solvents To a solution of 0.5 mmol of rac-2-amino-3-phenylpropionitrile (obtained from the HCl-salt by extraction of a basified aqueous solution) and 0.75 mmol of acyl donor in 5.0 ml of organic solvent (toluene, heptane, THF or MTBE) was added 90–100 mg of Novozym 435® or Acylase I (*Aspargillus melleus*). The reaction mixture was stirred at 60° C. for 40–66 h and analyzed in time by HPLC.

The following results were obtained with Novozym 435:

With methyl hexanoate as acyl donor in MTBE, N-hexanoyl-(S)-2-amino-3-phenylpropionitrile with e.e. 83% at 10% conversion. With methyl valerate as acyl donor in MTBE, N-valeryl-(S)-2-amino-3-phenylpropionitrile with e.e. 77% at 32% conversion. With methyl phenylacetate as acyl donor in toluene, N-phenylacetyl-(S)-2-amino-3-phenylpropionitrile with e.e.>99% at 15% conversion.

The best results with Acylase I were obtained with i-propyl acetate as acyl donor (in toluene or heptane) or with ethyl acetate as acyl donor (in toluene). In all cases N-acetyl-(R)-2-amino-3-phenylpropionitrile with e.e.>90% was formed in low conversion.

EXAMPLE 9

Resolution of rac-2-amino-3-phenylpropionitrile by enzymatic acylation in MTBE Catalyzed by Novozym 435®

To a solution of 7.3 g (50 mmol) of rac-2-amino-3-phenylpropionitrile and 11.3 g (75 mmol) of methyl phenylacetate in 500 ml of MTBE was added 1 0 g of Novozym 435®. The reaction mixture was stirred at 60° C. Initially every hour 10 ml of solvent was distilled to remove the methanol formed and replaced by 10 ml of fresh MTBE. After 29 h the reaction was stopped at 14% conversion. N-phenylacetyl-(S)-2-amino-3-phenylpropionitrile with e.e.>99% was obtained.

EXAMPLE 10

Hydrogenation of rac-2-amino-3-phenylpropionitrile.HCl-salt to the amino aldehyde To a solution of 9.0 g (49 mmol) of rac-2-amino-3-phenylpropionitrile.HCl-salt in 280 mL of water was added 2.2 equiv. of conc. HCl solution and 2.0 g of 5% Pd/C. The mixture was hydrogenated for 4.5 h at 35° C. and 2.0 MPa of hydrogen pressure. After filtration of the Pd catalyst, the solution was analyzed by HPLC and contained 86% of rac-2-amino-3-phenylpropionaldehyde.HCl-salt (as its hydrate). In addition 6% of 1,2-diamino-3-phenylpropane.2HCl-salt was formed and 7% of starting material was still present. This example illustrates a hydrogenation yielding a product with high amino aldehyde content and low diamine content.

EXAMPLE 11

Hydrogenation of (R)-2-amino-3-phenylpropionitrile.HCl-salt to the (R)-amino Alcohol To a solution of 9.0 g (49 mmol) of (R)-2-amino-3-phenylpropionitrile.HCl-salt (97.5% e.e.) in 280 mL of methanol-water 1:1 was added 2.2 equiv. of conc. HCl solution and 2.0 g of 5% Pd/C. The solution was hydrogenated for 19 h at 35° C. and 0.9 MPa of hydrogen pressure. Then additional 2 g of Pd/C was added and hydrogenation was continued for 24 h at 3.0 MPa. According to chiral HPLC 91% of (R)-2-amino-3-phenyl-1-propanol was formed together with 6% of (R)-3-phenyl-1,2-diaminopropane The reaction mixture was filtered and partially evaporated. The solution was basified to pH 10 using diluted NaOH solution and extracted with $CH_2CL_2$. The organic solution was dried over $Na_2SO_4$ and evaporated.

The hydrogenation was repeated 4 times under identical conditions. The combined residues were suspended in water and 5.0 g (40 mmol) of oxalic acid (1.2 eq based on the amount of amine) was added. The mixture was heated at 70° C. to a clear solution was obtained and left for crystallization. After filtration the free (R)-2-amino-3-phenyl-1-propanol was obtained in 61% yield. A second crop of product was isolated from the filtrate by repeating the crystallization from a minimum amount of water. In total 29.2 g (79%) of (R)-2-amino-3-phenyl-1-propanol was isolated with>98% e.e.

EXAMPLE 12

Hydrogenation of (S)-2-amino-4-methylvaleronitrile.HCl-salt to (S)-leucinol

To a solution of 3.0 g (20 mmol) of (S)-2-amino-4-methylvaleronitrile.HCl-salt (25% e.e.) in 100 mL of methanol-water 1:1 was added 2.2 equivalent of conc. HCl solution and 0.80 g of Pd/C. The solution was hydrogenated under vigorous stirring at 35° C. and 1.0 MPa of hydrogen pressure. After 5 h almost all starting material was converted and the hydrogenation was continued for 48 h at 5.0 MPa until most of the amino aldehyde was converted to the amino alcohol. The racemization free conversion to (S)-leucinol (25% e.e.) was 77%.

EXAMPLE 13

Hydrogenation of (R)-2-amino-3-methylbutyronitrile.HCl-salt to (R)-valinol

To a solution of 2.7 g (20 mmol) (R)-2-amino-3-methylbutyronitrile.HCl-salt (71% e.e.) in 100 mL of MeOH—$H_2O$ 1:1 was added 2.2 equiv. of conc. HCl solution and 0.80 g of Pd/C. The mixture was hydrogenated for 5 h and 1.0 MPa of hydrogen pressure under vigorous stirring. Then additional 0.40 g of Pd/C was added and the hydrogenation was continued for 23 h at 5.0 MPa until all the intermediate amino aldehyde was converted. (R)-valinol (71% e.e.) was formed without racemization in appr. 90% conversion, together with 6% of the corresponding 3-methyl-1,2-diaminobutane.

EXAMPLE 14

Hydrogenation of (R)-2-amino-2,3-dimethylbutyronitrile.HCl-salt to (R)-2-methylvalinol To a solution of 2.7 g (20 mmol) (R)-2-amino-2,3-dimethylbutyronitrile.HCl-salt (>89% e.e.) in 100 mL of MeOH—$H_2O$ 1:1 was added 2.2 equiv. of conc. HCl solution and 0.80 g of Pd/C. The mixture was hydrogenated for 5 h and 1.0 MPa of hydrogen pressure under vigorous stirring. Then additional 0.40 g of Pd/C was added and the hydrogenation was continued for 23 h at 5.0 MPa The conversion to (R)-2-methylvalinol (96% e.e.) was >90% and proceeded without racemization.

EXAMPLE 15

Hydrogenation of (R)-2-acetamido-3-phenylpropionitrile to (R)-2-acetamido-3-phenylpropionaldehyde To a solution of 3.78 g (20 mmol) of (R)-2-acetamido-3-phenylpropionitrile (e.e. 98%) in 110 ml of methanol-water 1:1 was added 1.1 equiv. of conc. HCl solution and 0.8 g of 5% Pd on carbon. The mixture was hydrogenated under vigorous stirring at 35° C. and 0.8 MPa of hydrogen pressure. After 2.5 h the hydrogenation was stopped and the catalyst was filtered. According to HPLC the remaining solution contained 85% of (R)-2-acetamido-3-phenylpropionaldehyde, together with 8% of the corresponding dimethyl acetal and 6% of N-acetyl-1,2-diamino-3-phenylpropane. The solution was neutralised to pH 7–8 with diluted NaOH solution and 8.3 g (80 mmol) of NaHSO$_3$ was added. After stirring for 2 h the solution was concentrated under reduced pressure. To the residue 200 ml of i-PrOH was added and the suspension was concentrated to 100 ml. After filtration and drying 11.5 g of a white solid was obtained containing 85% of the bisulfite addition product based on the starting material. This bisulfite addition product can be stored as a stable compound. (R)-2-acetamido-3-phenylpropionaldehyde was liberated from the bisulfite addition product by dissolving 0.5 g in 100 ml of water, basifying to pH 10 with diluted NaOH solution and extraction with 100 ml of ethyl acetate. The ethyl acetate layer contained the (R)-2-acetamido-3-phenylpropionaldehyde in 99% purity. The e.e. determined after further hydrogenation of (R)-2-acetamido-3-phenylpropionaldehyde in MeOH-water was >98% e.e.

EXAMPLE 16

Hydrogenation of (R)-2-(phenylacetamido)-3-methylbutyronitrile to (R)-2-(phenylacetamido)-3-methylbutyraldehyde in MeOH-water To a solution of 2.0 g (10 mmol) (R)-2-amino-3-methylbutyronitrile (94% e.e.) in 110 ml of MeOH—H$_2$O 1:1 was added 2.2 equiv. of conc. HCl solution and 0.45 g of Pd on carbon. The mixture was hydrogenated at 25° C. for 5 h and 1.0 MPa of hydrogen pressure under vigorous stirring. After filtration of the catalyst and neutralisation to pH 7.0 with diluted NaOH a solution was obtained containing the (R)-2-(phenylacetamido)-3-methylbutyraldehyde, together with some (R)-2-(phenylacetamido)-3-methylbutanol (after hydrolysis to valinol: e.e. 92% by HPLC) and (R)-2-(phenylacetamido)-3-methylbutylamine. To this solution 4.1 g (40 mmol) of NaHSO$_3$ was added. After stirring for 2 h the solution was concentrated under reduced pressure. To the residue 200 ml of i-PrOH was added and the suspension was concentrated to 100 ml. After filtration and drying 5.0 g of the bisulfite addition product was obtained as a white solid (62% based on the starting material). This bisulfite addition product can be stored as a stable compound.

EXAMPLE 17

Hydrogenation of (R)-2-(phenylacetamido)-3-methylbutyronitrile to (R)-2-(phenylacetamido)-3-methylbutyraldehyde in THF-water To a solution of 1.0 g (5 mmol) (R)-2-amino-3-methylbutyronitrile (94% e.e.) in 28 ml of tetrahydrofuran (THF) and 25 ml of H$_2$O 1:1 was added 2.2 equiv. of conc. HCl solution and 0.20 g of Pd on carbon. The mixture was hydrogenated at 25° C. for 3 h and 1.0 MPa of hydrogen pressure under vigorous stirring. After filtration of the catalyst, the solution was neutralised to pH 7.0 with diluted NaOH solution and 2.1 g (20 mmol) of NaHSO$_3$ was added. After stirring for 2 h the solution was concentrated under reduced pressure. To the residue was added 50 ml of i-PrOH and the suspension was concentrated to 25 ml. After filtration and drying 2.8 g of (R)-2-(phenylacetamido)-3-methylbutyraldehyde bisulfite addition product was obtained as a white solid, still containing salts.

The e.e. of (R)-2-(phenylacetamido)-3-methylbutyraldehyde was determined by HPLC after liberation of the bisulfite adduct, hydrogenation of the aldehyde to the alcohol and acidic hydrolysis to (R)-valinol (e.e. 91%).

The invention claimed is:

1. A process for the preparation of an enantiomerically enriched compound of formula 1

or a salt thereof, wherein:
C* represents an asymmetric carbon atom;
R$^1$ and R$^2$ are different from each other, and, each independently, represents H, a substituted or unsubstituted alkyl or aryl group;
R$^3$ represents CH$_2$OH or an optionally protected CHO group;
R$^5$ represents H, a substituted or unsubstituted alkyl or aryl group; and
R$^4$ represents H or C(=O)R$^6$ wherein R$^6$ represents H, a substituted or unsubstituted alkyl, aryl or alkoxy group, or R$^4$ represents or an amine protecting group, or R$^4$ and R$^5$ form together with the N to which they are attached a cyclic imide group, which process comprises hydrogenating an enantiomerically enriched compound of formula 2

or a salt thereof, wherein C*, R$^1$, R$^2$, and R$^5$ are as defined above; and
R$^7$ represents H or C(=O)R$^6$ wherein R$^6$ is as defined above, or R$^7$ represents an amine protecting group, or R$^5$ and R$^7$ form together with the N to which they are attached a cyclic imide group, in the presence of an aqueous solvent, hydrogen, a hydrogenation catalyst and a mineral acid.

2. The process of claim 1, wherein R$^3$ is an optionally protected CHO group and wherein hydrogen is present at a hydrogen-pressure between 0.1 and 2 MPa.

3. The process of claim 2, wherein the hydrogen-pressure is between 0.5 and 1 MPa.

4. The process of claim 1 further comprising transforming an amino aldehyde of formula 1 in situ into an N, N-dibenzylated, bisulfite adduct, acetal, oxime, hydrazone, cyanohydrine, or amino nitrile compound; and isolating the transformed compound.

5. The process of claim 1, wherein $R^3$ is a $CH_2OH$ group and wherein at least during part of the hydrogenation hydrogen is present at a hydrogen-pressure between 2 and 10 MPa.

6. The process of claim 5, wherein at least during part of the hydrogenation the hydrogen-pressure is between 4 and 6 MPa.

7. The process of claim 5, wherein the hydrogen-pressure initially is between 0.5 and 2 MPa and subsequently, after most of the compound of formula 2 is converted to the compound of formula 1, the hydrogen pressure is increased to a value between 2 and 10 MPa.

8. The process of claim 1, wherein the hydrogenation catalyst is a Pd catalyst.

9. The process of claim 1, wherein the compound of formula 2 is prepare by (precursor) fermentation, enzymatic resolution, crystallization induced asymmetric transformation, classical resolution, resolution via preferential crystallization, diastereomeric synthesis, catalytic asymmetric synthesis or dehydration of at least one amino acid amide.

10. The process of claim 1 further comprising isolating a salt of the amino aldehyde of formula 1 in the form of a hydrate, hemiacetal or acetal.

* * * * *